United States Patent
Landrith et al.

(10) Patent No.: US 11,771,924 B2
(45) Date of Patent: Oct. 3, 2023

(54) MAGNETORESISTIVE LINEAR POSITION DETECTION IN A RADIATION THERAPY SYSTEM

(71) Applicant: VARIAN MEDICAL SYSTEMS, INC., Palo Alto, CA (US)

(72) Inventors: Garrett Weston Landrith, San Jose, CA (US); Moussa Najib Iskandar, Fremont, CA (US); Michael William Weitzel, San Jose, CA (US); Chris McWilliams, Daly City, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/827,697

(22) Filed: May 28, 2022

(65) Prior Publication Data
US 2022/0362585 A1 Nov. 17, 2022

Related U.S. Application Data

(63) Continuation of application No. 17/072,042, filed on Oct. 16, 2020, now Pat. No. 11,344,749.

(51) Int. Cl.
*A61N 5/10* (2006.01)
*G01D 5/16* (2006.01)
*G21K 1/04* (2006.01)

(52) U.S. Cl.
CPC ......... *A61N 5/1075* (2013.01); *A61N 5/1045* (2013.01); *A61N 5/1047* (2013.01); *G01D 5/16* (2013.01); *G21K 1/046* (2013.01)

(58) Field of Classification Search
None
See application file for complete search history.

(56) References Cited

U.S. PATENT DOCUMENTS

| | | | |
|---|---|---|---|
| 2009/0080602 A1 | 3/2009 | Brooks et al. | |
| 2009/0080619 A1* | 3/2009 | Hasegawa | G21K 1/046 378/151 |
| 2010/0278310 A1 | 11/2010 | Dehler et al. | |
| 2012/0312961 A1 | 12/2012 | Raleigh et al. | |
| 2013/0284951 A1 | 10/2013 | Echner | |
| 2015/0352376 A1 | 12/2015 | Wiggers et al. | |
| 2016/0071623 A1 | 3/2016 | Schewiola et al. | |

(Continued)

FOREIGN PATENT DOCUMENTS

| | | |
|---|---|---|
| JP | 2004016563 A | 1/2004 |
| JP | 2009261690 A | 11/2009 |
| WO | 2012010507 A1 | 1/2012 |

OTHER PUBLICATIONS

International Search Report and Written Opinion of the International Searching Authority, International application No. PCT/US2021/055108, dated Jan. 31, 2022.

(Continued)

*Primary Examiner* — Hoon K Song
(74) *Attorney, Agent, or Firm* — SU IP CONSULTING

(57) ABSTRACT

A multileaf collimator includes a plurality of movable leaves for shaping a radiotherapy beam, wherein each leaf is independently movable in a same linear travel direction. Each leaf includes a linear array of magnets disposed on a measurement surface of the leaf and an array of magnetoresistive sensors that is disposed proximate the measurement surfaces of the leaves.

20 Claims, 15 Drawing Sheets

(56) References Cited

U.S. PATENT DOCUMENTS

| | | |
|---|---|---|
| 2016/0220223 A1 | 8/2016 | Kim et al. |
| 2018/0161602 A1 | 6/2018 | Kawrykow et al. |
| 2020/0061390 A1 | 2/2020 | Ma et al. |
| 2022/0118286 A1 | 4/2022 | Landrith et al. |
| 2022/0120588 A1 | 4/2022 | Iskandar et al. |

OTHER PUBLICATIONS

International Search Report and Written Opinion of the International Searching Authority, International application No. PCT/US2021/055109, dated Feb. 1, 2022.

* cited by examiner

MAGNETORESISTIVE LINEAR POSITION DETECTION IN A RADIATION THERAPY SYSTEM

CROSS-REFERENCE TO RELATED APPLICATIONS

The present application is a continuation under 35 U.S.C. § 120 of U.S. patent application Ser. No. 17/072,042, filed Oct. 16, 2020, which is related in subject matter to U.S. patent application Ser. No. 17/072,046, filed Oct. 16, 2020. The aforementioned U.S. patent applications are incorporated herein by reference.

BACKGROUND

Unless otherwise indicated herein, the approaches described in this section are not prior art to the claims in this application and are not admitted to be prior art by inclusion in this section.

Radiation therapy, which is the use of ionizing radiation, is a localized treatment for a specific target tissue, such as a cancerous tumor. Ideally, radiation therapy is performed on target tissue (also referred to as the planning target volume) in a way that spares the surrounding normal tissue from receiving doses above specified tolerances, thereby minimizing risk of damage to the normal tissue. Both conformal radiotherapy and intensity-modulated radiotherapy have been developed so that a prescribed dose is correctly supplied to the planning target volume during radiation therapy.

In conformal radiotherapy, radiotherapy beams can be shaped around the target tissue, for example with a beam-limiting device, to give a high radiation dose to a cancerous tumor while minimizing dosing to the surrounding healthy tissue. In intensity-modulated radiotherapy, the intensity of a radiation beam is modulated so that a prescribed radiation dose conforms more precisely to the three-dimensional shape of the tumor. Both conformal radiotherapy and intensity-modulated radiotherapy can greatly reduce the risk of side effects and/or enable increased dosing of target tissue.

A commonly used beam-limiting device in conformal and intensity-modulated radiation therapy is the multileaf collimator (MLC). Generally, an MLC in a radiation therapy system includes a plurality of movable "leaves" of radiation-stopping material that are independently positioned within the path of a radiotherapy beam. In this way, an MLC enables targeted beam shaping and/or variation of the intensity of the radiotherapy beam.

So that a prescribed dose is correctly supplied to a planning target volume during radiation therapy, an MLC and each of the individual leaves included in the MLC must be precisely positioned relative to the linear accelerator that provides the radiation therapy. However, there are numerous drawbacks to the radiation-tolerant position sensors currently employed to measure the MLC and MLC leaf positions. For example, electromechanical position sensors have repeatability and reliability issues due to wear over time. In addition, some electromechanical position sensors can be subject to gravity-related inaccuracy when positioned at certain angles, adding further uncertainty to the output of such sensors.

SUMMARY

In accordance with at least some embodiments of the present disclosure, a radiation therapy system is configured to measure a position of a multileaf collimator carousel and/or a position of an individual leaf in a multileaf collimator carousel using a magnetoresistive sensor. In some embodiments, a position of the multileaf collimator carousel is measured along an axis of linear motion via a linear array of magnets coupled to a surface of the carousel and a magnetoresistive sensor. In some embodiments, a position of an individual leaf in the multileaf collimator carousel is measured along an axis of linear motion via a linear array of magnets coupled to a surface of the leaf and a magnetoresistive sensor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
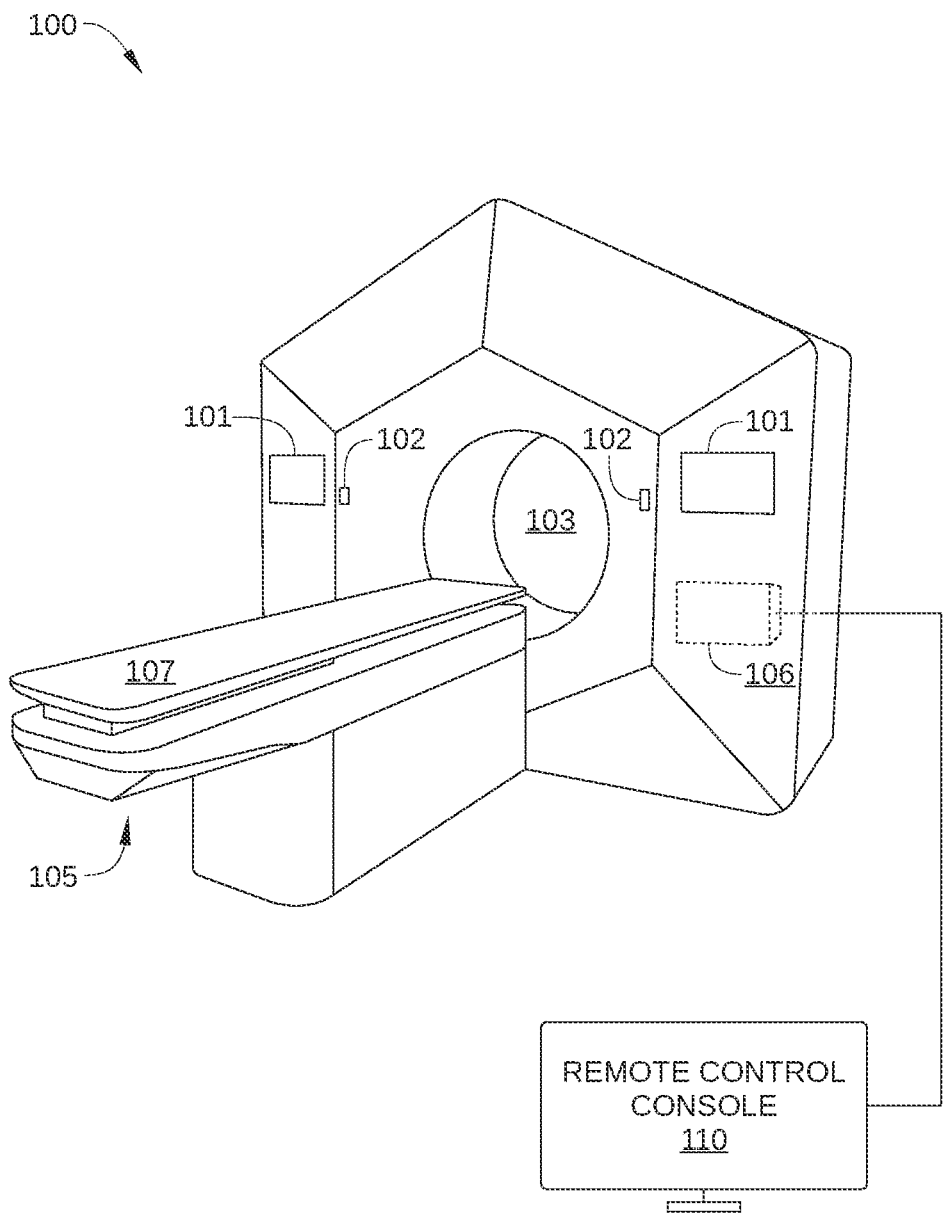
FIG. 1 is a perspective view of a radiation therapy system, according to one or more embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, beam shaping can play an important role in increasing the accuracy, efficiency, and quality of certain radiation treatments. To that end, multileaf collimators (MLCs) have been used in radiotherapy as beam shapers for conformal radiation therapy and as intensity modulators for intensity modulated radiotherapy (IMRT) and volumetrically modulated arc therapy (VMAT). In such therapies, accurate beam shaping depends on precise positioning of an MLC and the individual leaves in the MLC with respect to a treatment beam. According to various embodiments, improved and more reliable leaf positioning and MLC carousel positioning in a radiation therapy system is facilitated by measuring linear and/or rotational position with a magnetoresistive sensor as described below.

FIG. 1 is a perspective view of a radiation therapy system 100, according to one or more embodiments. Radiation therapy (RT) system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID) (not shown for clarity). Alternatively or additionally, RT system 100 can be configured to generate high-energy or very high-energy electrons, protons, heavy ions, and/or the like. By way of example, radiation therapy system 100 is described herein configured with a circular gantry. In other embodiments, RT system 100 can be configured with a C-gantry capable of infinite rotation via a slip ring connection or with a robotic arm.

Generally, RT system 100 is capable of kV imaging of a target volume during application of an MV treatment beam, so that an IMRT, VMAT, image-guided radiation therapy (IGRT) and/or conformal radiation therapy process can be performed. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
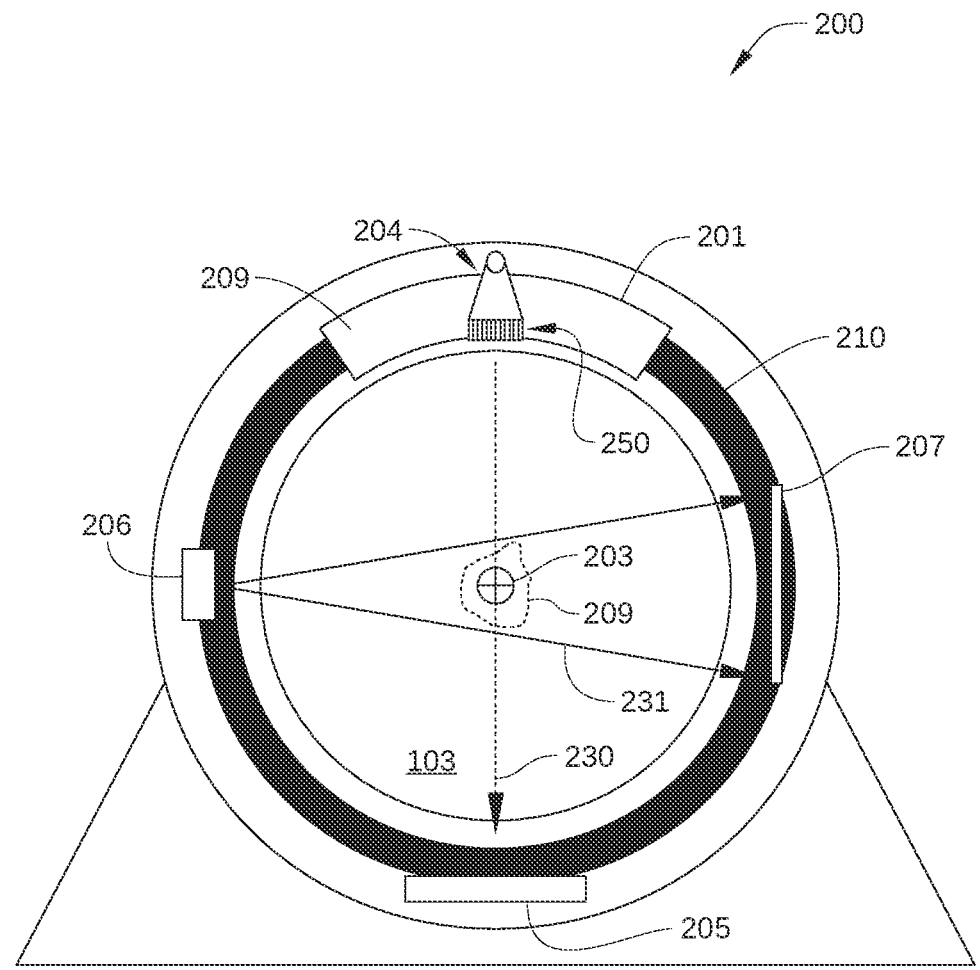
FIG. 2 schematically illustrates a drive stand and a gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 210 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, heavy ions, and/or the like) and EPID 205 is configured to acquire X-ray images via treatment beam 230. Imaging X-ray source 206 is configured to direct a conical beam of X-rays, referred to herein as imaging X-rays 231, through an isocenter 203 of RT system 100 to X-ray imager 207. Isocenter 203 typically corresponds to the location of the target volume to be treated. X-ray imager 207 receives imaging X-rays 231 and generates suitable projection images therefrom. Such projection images can then be employed to construct or update portions of imaging data for a digital volume that corresponds to a 3D region that includes the target volume. In some embodiments, conebeam computed tomography (CBCT) and digital tomosynthesis (DTS) can be used to process the projection images generated by X-ray imager 207.

In the embodiment illustrated in FIG. 2, X-ray imager 207 is depicted as a planar device. In other embodiments, X-ray imager 207 can have a curved configuration. In addition, in the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source.

LINAC 204 includes and/or is operated in conjunction with a collimator assembly 250. Collimator assembly 250 includes one or more collimators for shaping and/or modifying the intensity of MV treatment beam 230. One embodiment of collimator assembly 250 is described below in conjunction with FIG. 3.

Figure 3:
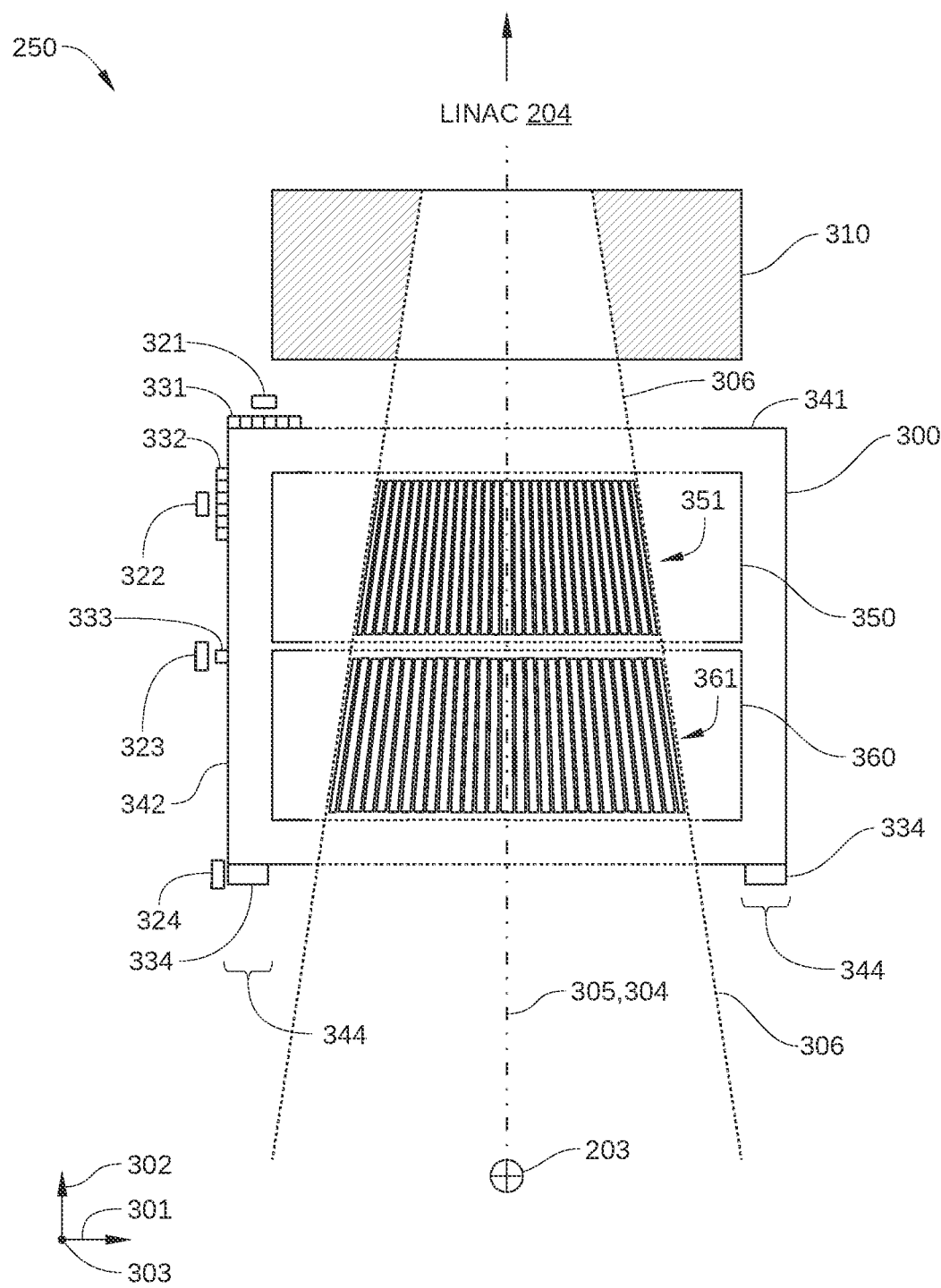
FIG. 3 schematically illustrates a collimator assembly of the radiation therapy system of FIG. 1, according to various embodiments.

FIG. 3 schematically illustrates collimator assembly 250, according to an embodiment. In the embodiment illustrated in FIG. 3, collimator assembly 250 includes a primary collimator 310 and an MLC carousel 300 that includes at least one MLC layer. Collimator assembly 250 is disposed proximate a radiation source (not shown) of LINAC 204 and between the radiation source and isocenter 203 of RT system 100. Further, in some embodiments, primary collimator 310 is fixed in position relative to the radiation source, while MLC carousel 300 is configured to be moved with respect to the radiation source. In some embodiments, MLC carousel 300 is configured to be translated along one or more linear axes, such as a first axis of linear motion 301, a second axis of linear motion 302, and/or a third axis of linear motion 303 (out of page). In some embodiments, MLC carousel 300 is configured to be rotated about at least one axis of rotation, such as an axis of rotation 304. In some embodiments, axis of rotation 304 is substantially parallel with a center line 305 of an X-ray field 306. In the instance illustrated in FIG. 3, axis of rotation 304 coincides with center line 305 of X-ray field 306, but in many instances, axis of rotation 304 is displaced from center line 305 along first axis of linear motion 301 and/or third axis of motion 303.

In some embodiments, MLC carousel 300 is configured with primary and secondary position detection for linear motion along first axis of linear motion 301, second axis of linear motion 302, third axis of linear motion 303, and/or axis of rotation 304. In some embodiments, primary motion detection with respect to one or more of the above axes is provided by a servo system associated with the motion. For example, in an embodiment, a servo system associated with linear motion of MLC carousel 300 along first axis of linear motion 301 includes certain position feedback that indicates the current position of MLC carousel 300 along first axis of linear motion 301. In such embodiments, such position feedback is considered primary linear position detection along axis of linear motion 301. In another example, in an embodiment, a servo system associated with rotational motion of MLC carousel 300 about axis of rotation 304 includes certain position feedback that indicates the current rotational position of MLC carousel 300 about axis of rotation 304. In such embodiments, such rotational position feedback is considered primary rotational position detection.

In some embodiments, motion detection with respect to one or more of the above axes (for example, secondary motion detection) is provided by a respective magnetoresistive sensor. Thus, in such embodiments, MLC carousel 300 includes one or more of: a magnetoresistive sensor 321 for motion detection of MLC carousel 300 with respect to first axis of linear motion 301; a magnetoresistive sensor 322 for motion detection of MLC carousel 300 with respect to second axis of linear motion 302, a magnetoresistive sensor 323 for motion detection of MLC carousel 300 with respect to third axis of linear motion 303, or a magnetoresistive sensor 324 for motion detection of MLC carousel 300 with respect to axis of rotation 304. In such embodiments, magnetoresistive sensor 321 performs motion detection via a linear array 331 of magnets disposed on a surface 341 of MLC carousel 300, magnetoresistive sensor 322 performs motion detection via a linear array 332 of magnets disposed on a surface 342 of MLC carousel 300, magnetoresistive sensor 323 performs motion detection via a linear array 333 of magnets disposed on surface 342 of MLC carousel 300, and/or magnetoresistive sensor 324 performs motion detection via a toothed ring 334 disposed on a peripheral region 344 of MLC carousel 300. In such embodiments, an International Electrotechnical Commission (IEC) requirement for a secondary position sensor is for all LINAC carousel linear and rotational axes can be satisfied by a respective magnetoresistive sensor.

One embodiment of a magnetoresistive sensor for linear motion detection of MLC carousel 300 is described below in conjunction with FIG. 4. One embodiment of a magnetoresistive sensor for rotational motion detection of MLC carousel 300 is described below in conjunction with FIG. 10.

Figure 4:
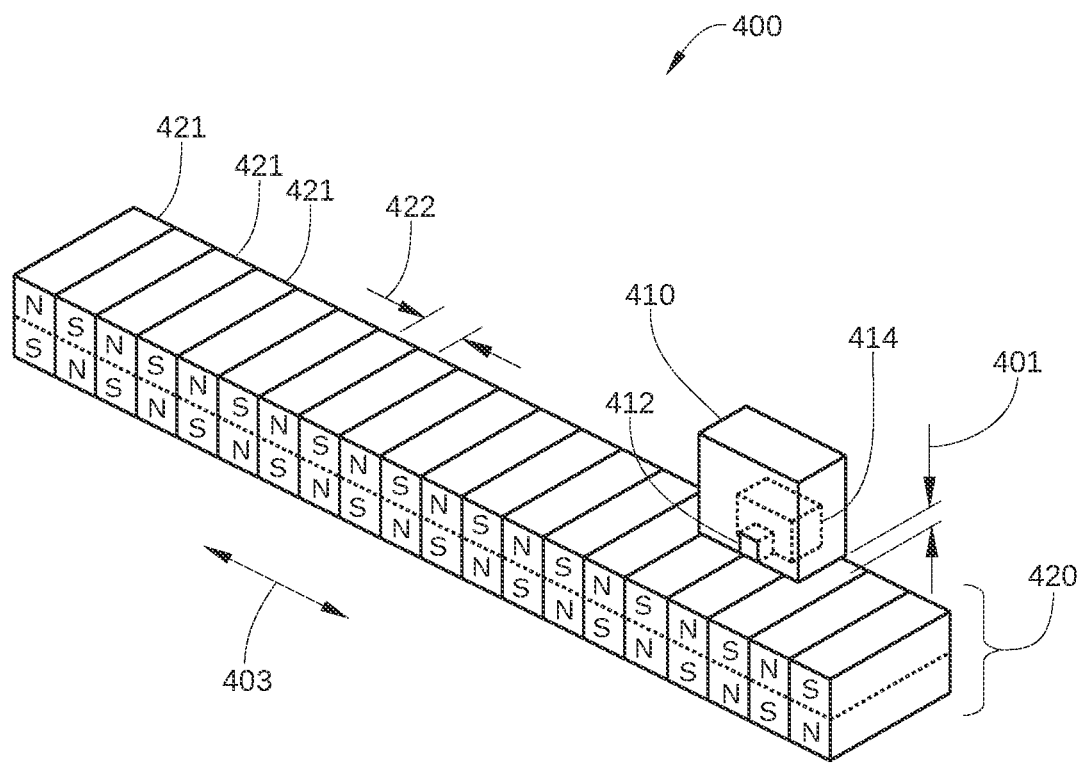
FIG. 4 schematically illustrates a linear motion detection apparatus, according to various embodiments.

FIG. 4 schematically illustrates a linear motion detection apparatus 400, according to various embodiments of the invention. In the embodiment illustrated in FIG. 4, linear motion detection apparatus 400 includes a magnetoresistive sensor 410 and a linear array 420 of magnets 421. In some embodiments, linear array 420 is implemented as a magnetic scale of magnets 421 of alternating poles (i.e., N-S-N-S and so on), where magnets 421 are each separated from each other with a uniform pole pitch 422.

Magnetoresistive sensor 410 is disposed proximate to and is separated from linear array 420 by an air gap 401. Thus, magnetoresistive sensor 410 is not physically in contact with linear array 420. As a result, neither magnetoresistive sensor 410 nor linear array 420 undergoes mechanical wear during use.

As shown, linear array 420 is configured as a linear array of magnets 421 that is longitudinally oriented in a particular linear travel direction 403. Magnetoresistive sensor 410 is configured to detect motion of linear array 420 relative to magnetoresistive sensor 410 in linear travel direction 403 and/or to generate position information that enables detection of motion of linear array 420 relative to magnetoresistive sensor 410 in travel direction 403. In some embodiments, magnetoresistive sensor 410 includes a magnetoresistive device 412, a bias magnet 414, and a resistive bridge (not shown). In some embodiments, the resistive bridge is included in magnetoresistive device 412. In some embodiments, magnetoresistive device 412 includes at least one of an anisotropic magnetoresistive (AMR) sensor, a giant magnetoresistive (GMR) sensor, a tunnel magnetoresistive (TMR) sensor, or other magnetic position sensor that measures changes in a magnetic field that occur when magnets 421 of linear array 420 move relative to magnetoresistive sensor 410.

Magnetoresistive sensor 410 generates position information based on the magnetoresistive effect, where an external magnetic field affects the electrical resistance of a magnetoresistive material in magnetoresistive sensor 410. For example, in some embodiments, magnetoresistive sensor 410 is configured to operate as a sine encoder that generates position information of magnets 421 in the form of a sine output signal and a cosine output signal that are based on the current angle of a magnetic field. Based on the sine output signal and the cosine output signal, a position of magnetoresistive sensor 410 between two adjacent magnets 421 can be determined. In such embodiments, the sine and cosine output signals enable precise determination of the position of magnetoresistive sensor 410 between two adjacent magnets 421. For example, in an embodiment in which magnetoresistive sensor 410 is configured to generate signals for resolving a position of magnetoresistive sensor 410 to within 1° (where pole pitch 422 equates to 360°), the position of magnetoresistive sensor 410 can be determined to within a fraction of 1% of pole pitch 422. Thus, magnetoresistive sensor 410 can provide precise position information regarding linear array 420 relative to magnetoresistive sensor 410.

It is noted that magnetoresistive sensor 410 does not actively generate a position signal, and instead is a passive device. As a result, the output of magnetoresistive sensor 410 is generally unaffected by the high-radiation environment of an X-ray field present in a radiation therapy system, such as X-ray field 306 in FIG. 3.

Returning to FIG. 3, primary collimator 310 is configured to define an outer limit of X-ray field 306. Primary collimator 310 can be a fixed collimator or a collimator configured with one or more movable jaws. Typically, primary collimator 310 is disposed proximate the radiation source of LINAC 204. In the embodiment illustrated in FIG. 3, primary collimator 310 is depicted as a single collimating apparatus, but in other embodiments, primary collimator 310 includes multiple collimating apparatuses positioned in series within X-ray field 306.

In some embodiments, MLC carousel 300 includes a proximal MLC layer 350 and a distal MLC layer 360. In other embodiments, MLC carousel 300 includes a single MLC layer. Proximal MLC layer 350 includes a plurality of leaves 351 that are each independently movable into X-ray field 306 in a travel direction. Similarly, distal MLC layer 360 includes a plurality of leaves 361 that are each independently movable into X-ray field 306 in a travel direction. In the embodiment illustrated in FIG. 3, each leaf 351 of proximal MLC layer 350 is movable in one particular travel direction, which is perpendicular to center line 305 of X-ray field 306. Further, in the embodiment illustrated in FIG. 3, the travel direction of leaves 351 is depicted to be along third axis of linear motion 303, which is out of the page. Similarly, each leaf 361 of distal MLC layer 360 is movable in one particular travel direction that is perpendicular to center line 305 of X-ray field 306. In the embodiment illustrated in FIG. 3, the travel direction of leaves 361 is the same travel direction as that of leaves 351, which is along axis of linear motion 303. In FIG. 3, leaves 351 and leaves 361 are viewed end-on, i.e., along the travel direction, which is parallel to third axis of linear motion 303.

In some embodiments, proximal MLC layer 350 includes multiple banks of leaves 351 and distal MLC layer 360 includes multiple banks of leaves 361. In such embodiments, MLC layer 350 includes two opposing banks of leaves 351 that are positioned on opposite sides of a center plane of X-ray field 306, and distal MLC layer 360 includes two opposing banks of leaves 361 that are positioned on opposite sides of the center plane of X-ray field 306.

Leaves 351 and 361 are typically formed from a high atomic number material, such as tungsten or an alloy thereof. In addition, in some embodiments, leaves 351 and 361 have a generally trapezoidal cross-section that matches the beam divergence that occurs in the direction perpendicular to leaf travel. In practice, the cross-section of leaves 351 and 361 may not exactly trapezoidal. In some embodiments, leaves 351 and leaves 361 may be configured to project to a same projected size at isocenter 203. In such embodiments, leaves 351 have a smaller cross-section in the direction perpendicular to leaf travel than leaves 361.

In some embodiments, motion detection of each of leaves 351 and leaves 361 along a direction of linear travel is enabled by a respective magnetoresistive sensor. In such embodiments, each leaf 351 and each leaf 361 includes a magnetoresistive sensor for linear motion detection of the corresponding leaf. One such embodiment is described below in conjunction with FIG. 5.

Figure 5:
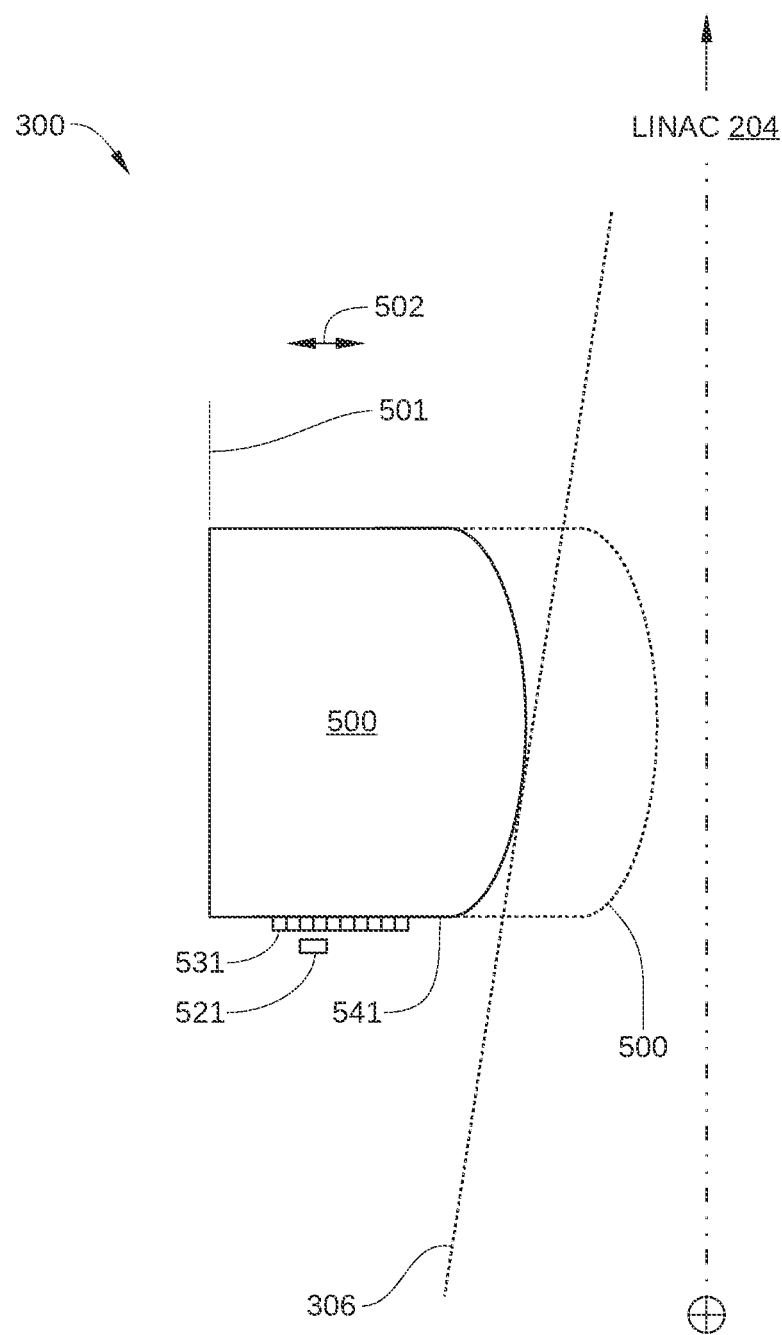
FIG. 5 schematically illustrates a side view of a single leaf the of collimator assembly of FIG. 3, according to various embodiments.

FIG. 5 schematically illustrates a side view of a single leaf 500 of MLC carousel 300, according to various embodiments. As shown, leaf 500 is positioned at a beginning edge 501 of a travel range in a particular direction of travel 502, and is therefore disposed proximate to but outside X-ray field 306. Leaf 500 is also shown (dashed lines) after traveling partially along the travel range in the direction of travel 502.

Leaf 500 includes a magnetoresistive sensor 521 and a linear array 531 of magnets disposed on an edge surface 541 of leaf 500. In some embodiments, magnetoresistive sensor 521 can be consistent in configuration with one or more embodiments of magnetoresistive sensor 410 in FIG. 4 and linear array 531 can be consistent in configuration with one or more embodiments of linear array 420 in FIG. 4.

In operation, as leaf 500 moves along direction of travel 502, magnetoresistive sensor 521 generates position information for precisely determining a current position of magnetoresistive sensor 521 between the two closest magnets included in linear array 531. In some embodiments, magnetoresistive sensor 521 generates such position information in the form of a sine output signal and a cosine output signal. In some embodiments, such position information is employed for secondary motion detection of leaf 500 along direction of travel 502. In such embodiments, a servo system associated with moving leaf 500 along direction of travel 502 provides primary linear motion detection. Thus, in such embodiments, an IEC requirement for all moving leaves in a radiation therapy system to have both primary and secondary position sensors is satisfied.

Figure 6:
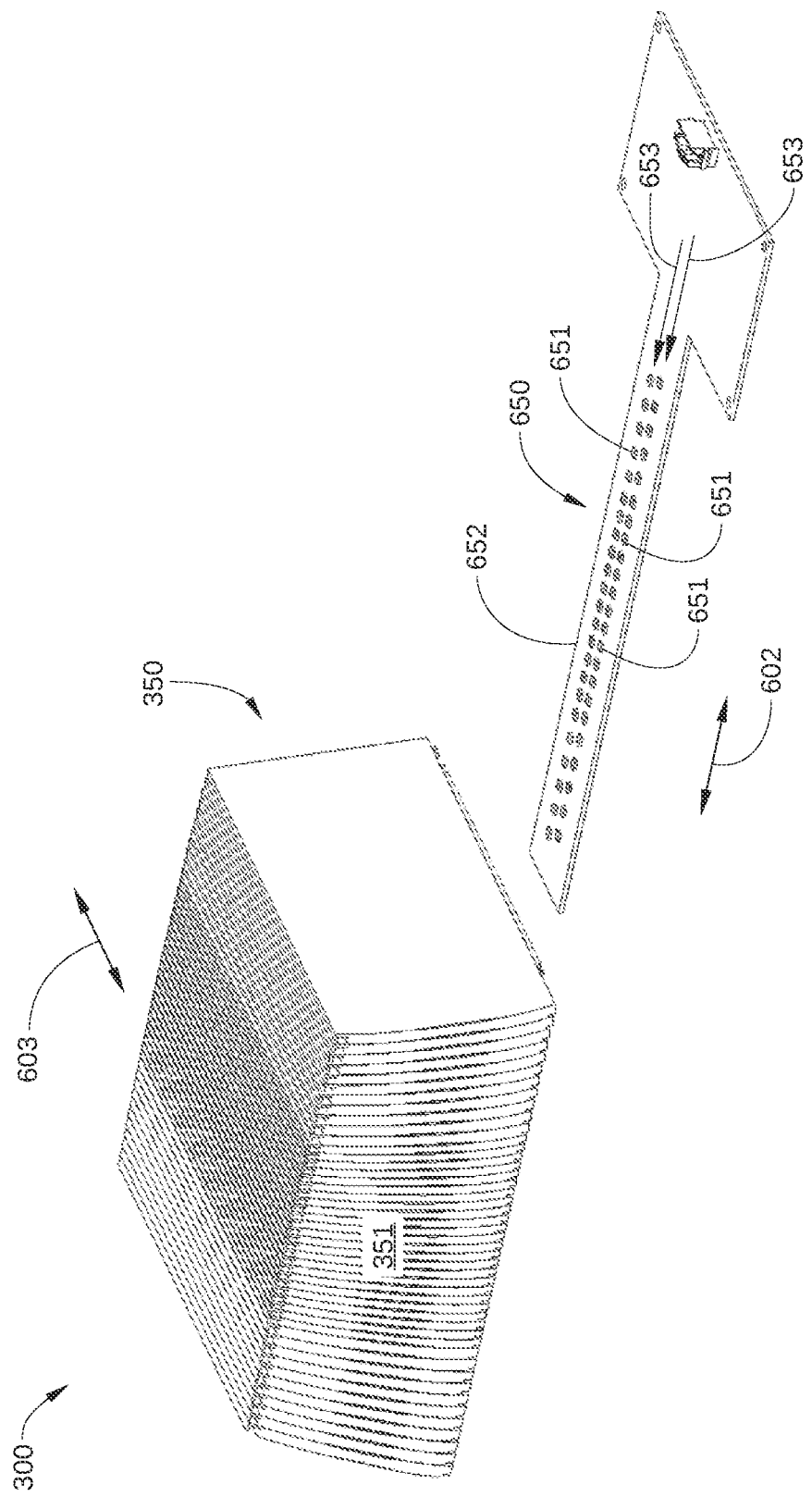
FIG. 6 is a perspective view of a multileaf collimator carousel of the radiation therapy system of FIG. 1, according to an embodiment.

FIG. 6 is a perspective view of MLC carousel 300, according to an embodiment. In FIG. 6, an array 650 of magnetoresistive sensors 651 for proximal MLC layer 350 is shown exploded from MLC carousel 300. In the embodiment illustrated in FIG. 6, magnetoresistive sensors 651 are disposed on a printed circuit board (PCB) 652. In some embodiments, array 650 of magnetoresistive sensors 651 is configured as a linear array that extends longitudinally in a direction 602 that is perpendicular to a linear travel direction 603 of leaves 351. In the embodiment illustrated in FIG. 6, array 650 includes multiple rows 653 of magnetoresistive sensors 651. In some embodiments, magnetoresistive sensors 651 in multiple rows 653 are staggered, so that magnetoresistive sensors 651 can be more closely spaced along direction 602. Insertion of PCB 652 into MLC carousel 300 causes each of magnetoresistive sensors 651 to be disposed proximate a measurement surface of a respective leaf 351 of proximal MLC layer 350.

Figure 7:
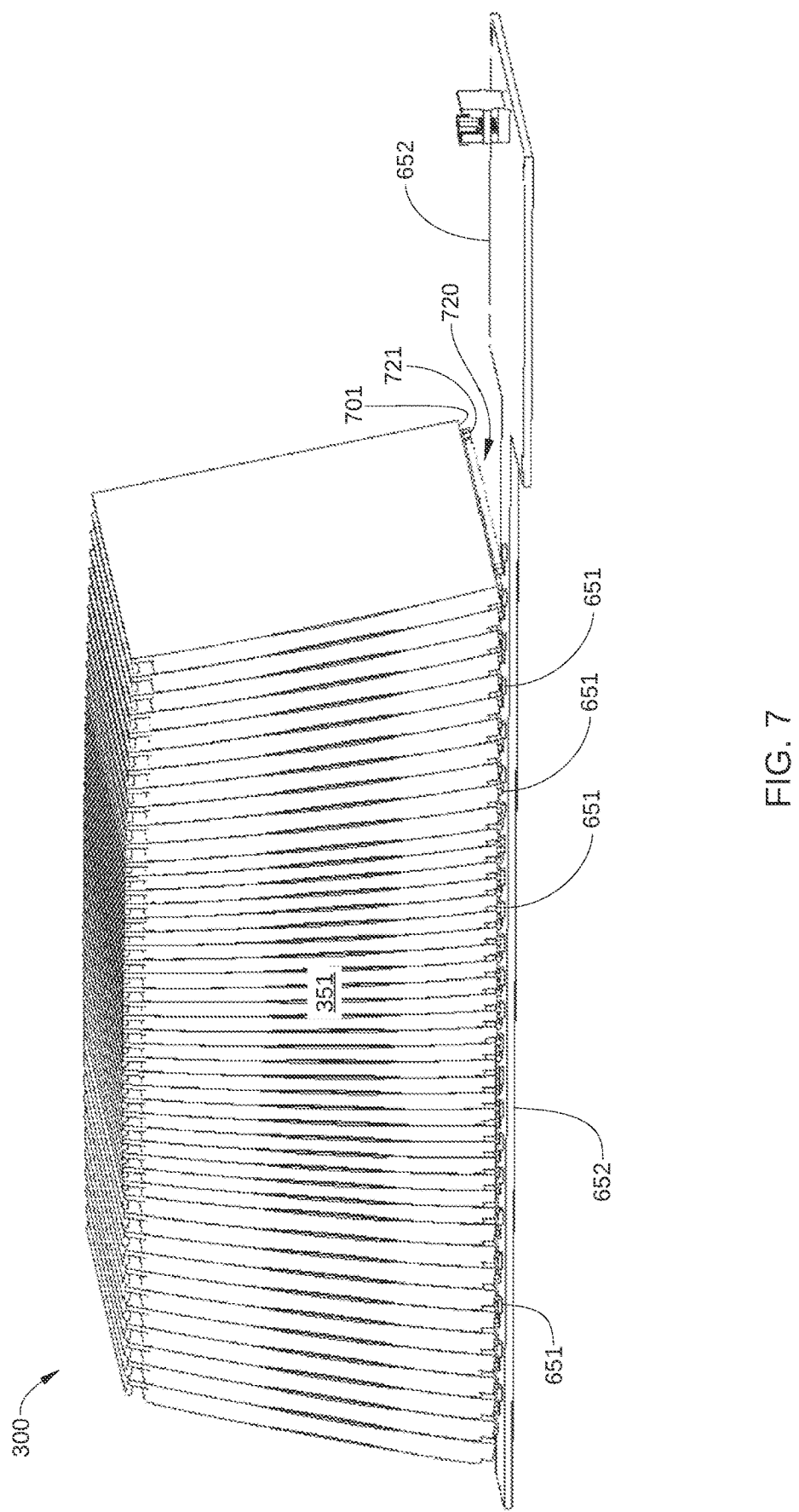
FIG. 7 is a perspective view of a printed circuit board when inserted into the multileaf collimator carousel of FIG. 6, according to an embodiment.

FIG. 7 is a perspective view of PCB 652 when inserted into MLC carousel 300, according to an embodiment. In FIG. 7, portions of MLC carousel 300 are omitted for clarity, such as a housing that encloses leaves 351. As shown, magnetoresistive sensors 651 are arranged on PCB 652 so that each of magnetoresistive sensors 651 is disposed proximate a measurement surface 701 of a respective leaf 351 of proximal MLC layer 350. In the embodiment illustrated in FIG. 7, each measurement surface 701 is an edge surface of a leaf 351 and each measurement surface 702 is an edge surface of a leaf 361. In the embodiment illustrated in FIG. 7, PCB 652 are configured to position magnetoresistive sensors 651 proximate magnets 721 on measurement surfaces 701 of leaves 351. In other embodiments, magnetoresistive sensors 651 are disposed on any other suitable surface of MLC carousel 300 that positions magnetoresistive sensors 651 proximate measurement surfaces 701 of leaves 351.

Figure 8:
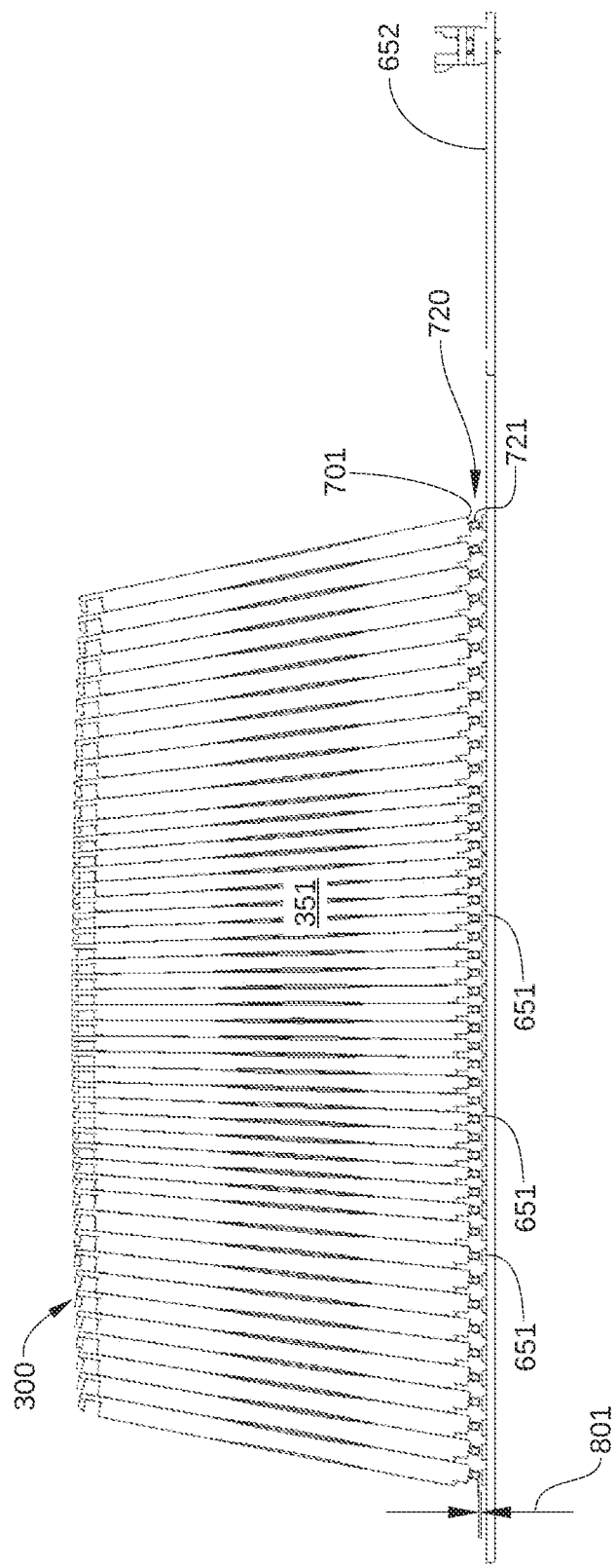
FIG. 8 is an end view of the multileaf collimator carousel of FIG. 6, according to an embodiment.

FIG. 8 is an end view of MLC carousel 300 when PCB 652 is inserted into MLC carousel 300, according to an embodiment. In FIG. 8, portions of MLC carousel 300 are omitted for clarity, such as a housing that encloses leaves 351. As shown, each linear array 720 (viewed end on in FIG. 8) of magnets 721 is separated from a corresponding magnetoresistive sensor 651 by an air gap 801. An embodiment of the configuration of magnets 721, air gap 801, leaves 351, and magnetoresistive sensors 651 is described below in conjunction with FIG. 9.

Figure 9:
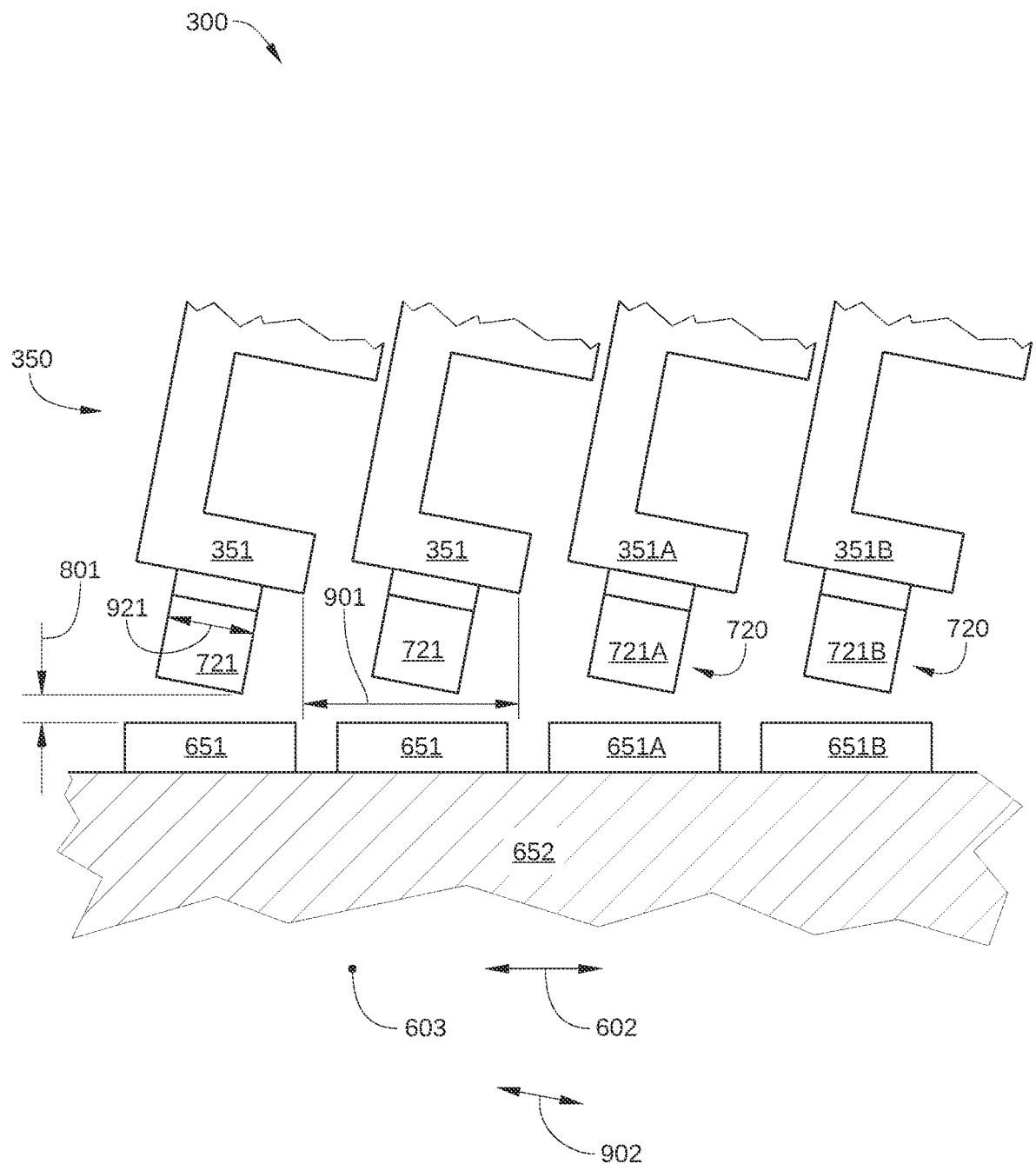
FIG. 9 is a partial end view of a multileaf collimator layer and a printed circuit board, according to an embodiment.

FIG. 9 is a partial end view of proximal MLC layer 350 and PCB 652, according to an embodiment. As shown, leaves 351 of MLC layer 350 are spaced apart in direction 602 by a leaf pitch 901, which is the on-center spacing (also referred to as the center-to-center distance) between two adjacent leaves 351. In the embodiment illustrated in FIG. 9, direction 602 is perpendicular to linear travel direction 603 of leaves 351, and linear travel direction 603 is oriented into and out of the page. Leaf pitch 901 is typically selected based on a desired functionality of the radiotherapy system that includes MLC carousel 300. In some embodiments, each magnetoresistive sensor 651 on PCB 652 is also spaced apart from adjacent magnetoresistive sensors 651 by leaf pitch 901. Air gap 801 separating each linear array 720 of magnets 721 from a corresponding magnetoresistive sensor 651 is shown.

In some embodiments, to reduce crosstalk between magnetoresistive sensors 651 of proximal MLC layer 350, a width 921 of a particular magnet 721 in a direction perpendicular to linear travel direction 603 is selected to be equal to or less than a threshold value. In some instances, the direction perpendicular to linear travel direction 603 is direction 602, and in other embodiments, the direction perpendicular to linear travel direction 603 is another direction, such as a direction 902 that is also perpendicular to a length of the leaf 351 to which the particular magnet 721 is coupled. In some embodiments, the threshold value may be based on leaf pitch 901, air gap 801, a field strength of the particular magnet 721, and/or one or more other factors associated with the configuration of proximal MLC layer 350, such as the size, relative position, and/or orientation of the particular magnet 721, magnetoresistive sensors 651, and the like. For example, in one such embodiment, the threshold value for width 921 of the particular magnet 721 is one half of leaf pitch 901. In another such embodiment, the threshold value for width 921 of the particular magnet 721 is determined based on a size of leaf pitch 901 and a size of air gap 801. In yet another such embodiment, the threshold value for width 921 of the particular magnet 721 is determined based on a minimum distance between the particular magnet 721 and an adjacent magnetoresistive sensor 651.

It is noted that when width 921 of magnets 721 is equal to or less than such a threshold value, crosstalk between adjacent magnetoresistive sensors 651 is reduced due to a greater distancing between magnets 721 coupled to one of leaves 351 and the magnetoresistive sensor 651 associated with an adjacent leaf 351. For example, when width 921 of magnets 721 is reduced, magnet 721A of leaf 351A is located farther from the magnetoresistive sensor 651B that is associated with adjacent leaf 351B. As a result, magnetoresistive sensor 651B is less likely to erroneously detect motion of leaf 351A. In the same vein, reduction in width 921 of magnet 721B results in magnetoresistive sensor 651A being less likely to erroneously detect motion of leaf 351B.

In some embodiments, to reduce crosstalk between magnetoresistive sensors 651 of proximal MLC layer 350, each magnet 721 in a particular linear array 720 is separated by a pole pitch (not visible in FIG. 9) that is selected to be equal to or less than a threshold value. An example of pole pitch in a linear array of magnets is illustrated as pole pitch 422 in FIG. 4. In some embodiments, the threshold value may be based on leaf pitch 901, air gap 801, a field strength of the magnets 721 included in the particular linear array 720, and/or one or more other factors associated with the configuration of proximal MLC layer 350, such as the size, width, relative position, and/or orientation of the magnets 721 included in the particular linear array 720, magnetoresistive sensors 651, and the like. For example, in some embodiments, the threshold value for the pole pitch separating magnets 721 in the particular linear array 720 is based on leaf pitch 901. In one such embodiment, the threshold value for the pole pitch separating magnets 721 in the particular linear array 720 is equal to or less than leaf pitch 901. In another such embodiment, the threshold value for the pole pitch separating magnets 721 in the particular linear array 720 is equal to or less than a specified fraction of leaf pitch 901.

In some embodiments, to reduce crosstalk between magnetoresistive sensors 651 of proximal MLC layer 350, each magnet 721 in a particular linear array 720 is configured with a field strength that is selected to be equal to or less than a threshold value. In some embodiments, the threshold value may be based on leaf pitch 901, air gap 801, and/or one or more other factors associated with the configuration of proximal MLC layer 350, such as the size, width, relative position, and/or orientation of the magnets 721 included in the particular linear array 720, magnetoresistive sensors 651, and the like. Thus, in some embodiments, the threshold value for the field strength of magnets 721 in the particular linear array 720 is selected to have a field strength that, when measured by a magnetoresistive sensor 651 associated with an adjacent leaf 351, is no greater than a particular fraction (e.g., 20%) of a field strength measured by the magnetoresistive sensor 651 associated with an adjacent leaf 351 for magnets coupled to the adjacent leaf 351. For example, in one such embodiment, a field strength for magnet 721A of leaf 351A measured by magnetoresistive sensor 651B is selected to be no greater than a particular fraction of the field strength for magnet 721B when measured by magnetoresistive sensor 651B. In such embodiments, the likelihood of a magnetoresistive sensor 651 erroneously measuring movement of magnets 721 coupled to an adjacent leaf 351 is greatly reduced or eliminated.

Figure 10:
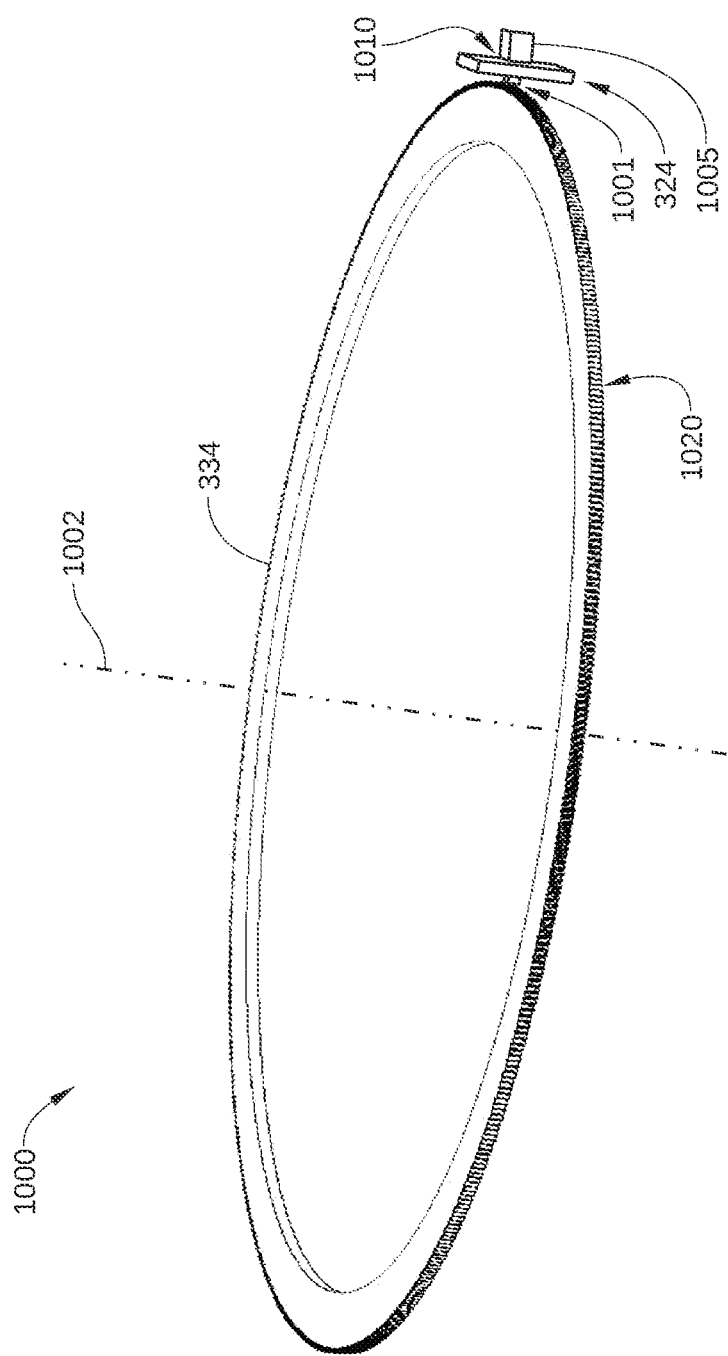
FIG. 10 schematically illustrates a linear rotational motion detection apparatus, according to various embodiments.

FIG. 10 schematically illustrates a linear rotational motion detection apparatus 1000, according to various embodiments. In the embodiment illustrated in FIG. 10, rotational motion detection apparatus 1000 includes magnetoresistive sensor 324 and toothed ring 334, which is disposed on peripheral region 344 of MLC carousel 300, as shown in FIG. 3. Toothed ring 334 includes an array of ferromagnetic gear teeth 1020. In some embodiments, magnetoresistive sensor 324 performs secondary (or primary) rotational motion detection by detecting a position of magnetoresistive sensor 324 relative to ferromagnetic gear teeth 1020 included in toothed ring 334.

In the embodiment illustrated in FIG. 10, magnetoresistive sensor 324 includes a bias magnet 1005 coupled to a magnetoresistive device 1010. Magnetoresistive device 1010 is configured to generate position information regarding the one or two ferromagnetic gear teeth 1020 that are currently proximate magnetoresistive sensor 324. Magnetoresistive device 1010 is disposed proximate to ferromagnetic gear teeth 1020 and is separated from ferromagnetic gear teeth 1020 by an air gap 1001. Thus, magnetoresistive device 1010 is not physically in contact with ferromagnetic gear teeth 1020. As a result, neither magnetoresistive device 1010 nor ferromagnetic gear teeth 1020 undergo mechanical wear during use.

In operation, as toothed ring 334 rotates with MLC carousel 300 (not shown), magnetoresistive sensor 324 generates rotational position information for precisely determining a current rotational position of magnetoresistive sensor 324 between the two closest ferromagnetic gear teeth 1020 included in toothed ring 334. In some embodiments, magnetoresistive sensor 324 generates such position information in the form of a sine output signal and a cosine output signal. In some embodiments, such position information is employed for secondary motion detection of toothed ring 334 (and consequently MLC carousel 300) about an axis of rotation 1002. In such embodiments, a servo system associated with rotating MLC carousel 300 about axis of rotation 1002 provides primary linear motion detection. Thus, in such embodiments, an IEC requirement for all rotational axes of an MLC carousel in a radiation therapy system to have both primary and secondary position sensors is satisfied.

Ideally, when position information in the form of a sine output signal and a cosine output signal are generated by magnetoresistive sensor 324, the sine output signal and cosine output signal are each centered around the same value. For example, in an instance in which magnetoresistive sensor 324 includes a 5 V supply, the sine output signal and the cosine output signal are each ideally centered at 2.5 V and vary in amplitude from 0 V to 5 V over a single cycle. However, in practice, various factors typically produce a signal offset from an ideal output value, which can result in an inaccurate rotational position measurement for toothed ring 334. One such instance is described below in conjunction with FIG. 11.

Figure 11:
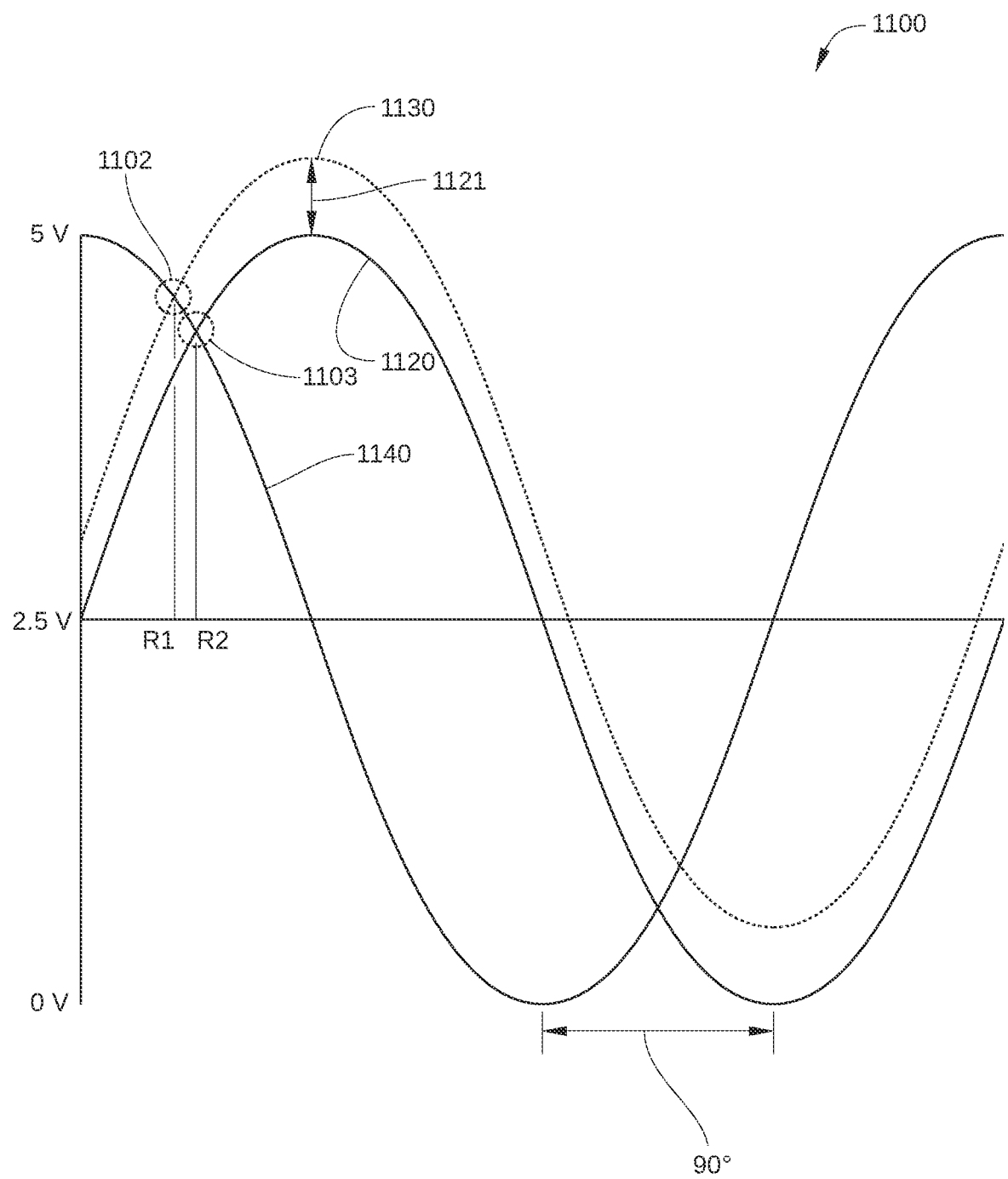
FIG. 11 is a graph illustrating output values for an ideal sine output signal, an actual sine output signal, and a cosine output signal from a magnetoresistive sensor.

FIG. 11 is a graph 1100 illustrating output values for an ideal sine output signal 1120, an actual sine output signal 1130, and a cosine output signal 1140 from magnetoresistive sensor 324. As shown, ideal sine output signal 1120 and cosine output signal 1130 each vary from 0 V to 5 V, and ideal sine output signal 1120 is out of phase from cosine output signal 1140 by 90°. In embodiments in which rotation of toothed ring 334 (shown in FIG. 10) from one ferromagnetic gear tooth 1020 to an adjacent ferromagnetic gear tooth 1020 corresponds to a single 360° cycle of magnetoresistive sensor 324, the 90° by which ideal sine output signal 1120 is out of phase from cosine output signal 1140 corresponds to ¼ of the rotational displacement between the two adjacent ferromagnetic gear teeth 1020. Based on the 90° phase offset between a sine output signal and a cosine output signal generated by magnetoresistive sensor 324, a precise position of magnetoresistive sensor between two adjacent ferromagnetic gear teeth 1020 of toothed ring 334 is determined.

In practice, the sine and cosine output signals generated by magnetoresistive sensor 324 are not ideal. For example, the sine and cosine output signals generated by magnetoresistive sensor 324 typically include a signal offset. For example, in the case of the sine output signal, a signal offset 1121 is present between ideal sine output signal 1120 and actual sine output signal 1130. As shown, signal offset 1121 causes an output value of actual sine output signal 1130 to cross over the output value of cosine output signal 1140 at an actual crossover point 1102. In the instance depicted in FIG. 11, signal offset 1121 is depicted as approximately +0.5 V, but in practice is typically much smaller. Actual crossover point 1102 occurs at a different rotational position R1 than an ideal crossover point 1103, which occurs at rotational position R2. The difference between rotational position R1 and rotational position R2 corresponds to an inaccuracy in the phase shift between the sine output signal and the cosine output signal generated by magnetoresistive sensor 324. As a result, when determining a rotational position of magnetoresistive sensor 324 between two adjacent ferromagnetic teeth 1020 based on actual sine output signal 1130 and cosine output signal 1140, the determined rotational position may be inaccurate. Factors that can contribute to and/or cause signal offset 1121 include variations in the resistance of resistors included in a resistive bridge of magnetoresistive sensor 324, other artifacts of the electronics included in magnetoresistive sensor 324, and/or physical tooth-to-tooth variations of ferromagnetic teeth 1020.

According to various embodiments, a calibration process is performed to determine a first signal offset value for a sine output signal generated by magnetoresistive sensor 324 and a second signal offset value for a cosine output signal generated by magnetoresistive sensor 324. In the embodiments, one or more dummy cycles are performed to enable quantification of the first and second signal offset values. The first and second signal offset values can then be employed to compensate for the inaccuracy in rotational position that otherwise results from non-ideal sine output signals and cosine output signals generated by magnetoresistive sensor 324.

In some embodiments, in a dummy cycle, an excitation is applied to an actuator for rotating toothed ring 334 so that toothed ring 334 rotates a specified rotational displacement, such as the rotational displacement between two adjacent ferromagnetic teeth 1020. In some embodiments, the specified rotational displacement corresponds to a rotational displacement of toothed ring 334 in which a first ferromagnetic tooth 1020 proximate magnetoresistive sensor 324 is rotated from a first rotational position to a second rotational position and a second ferromagnetic tooth 1020 that is adjacent to the first ferromagnetic tooth 1020 is rotated from the second rotational position to a third rotational position. Thus, over specified rotational displacement, the first ferromagnetic tooth 1020 moves to the position occupied by the second ferromagnetic tooth 1020 at the beginning of the cycle. Thus, during a dummy cycle, values are collected for a sine output signal and a cosine output signal generated by magnetoresistive sensor 324 as toothed ring 334 rotates through a rotational displacement that corresponds to one tooth pitch of toothed ring 334. One such embodiment is described below in conjunction with FIG. 12.

Figure 12:
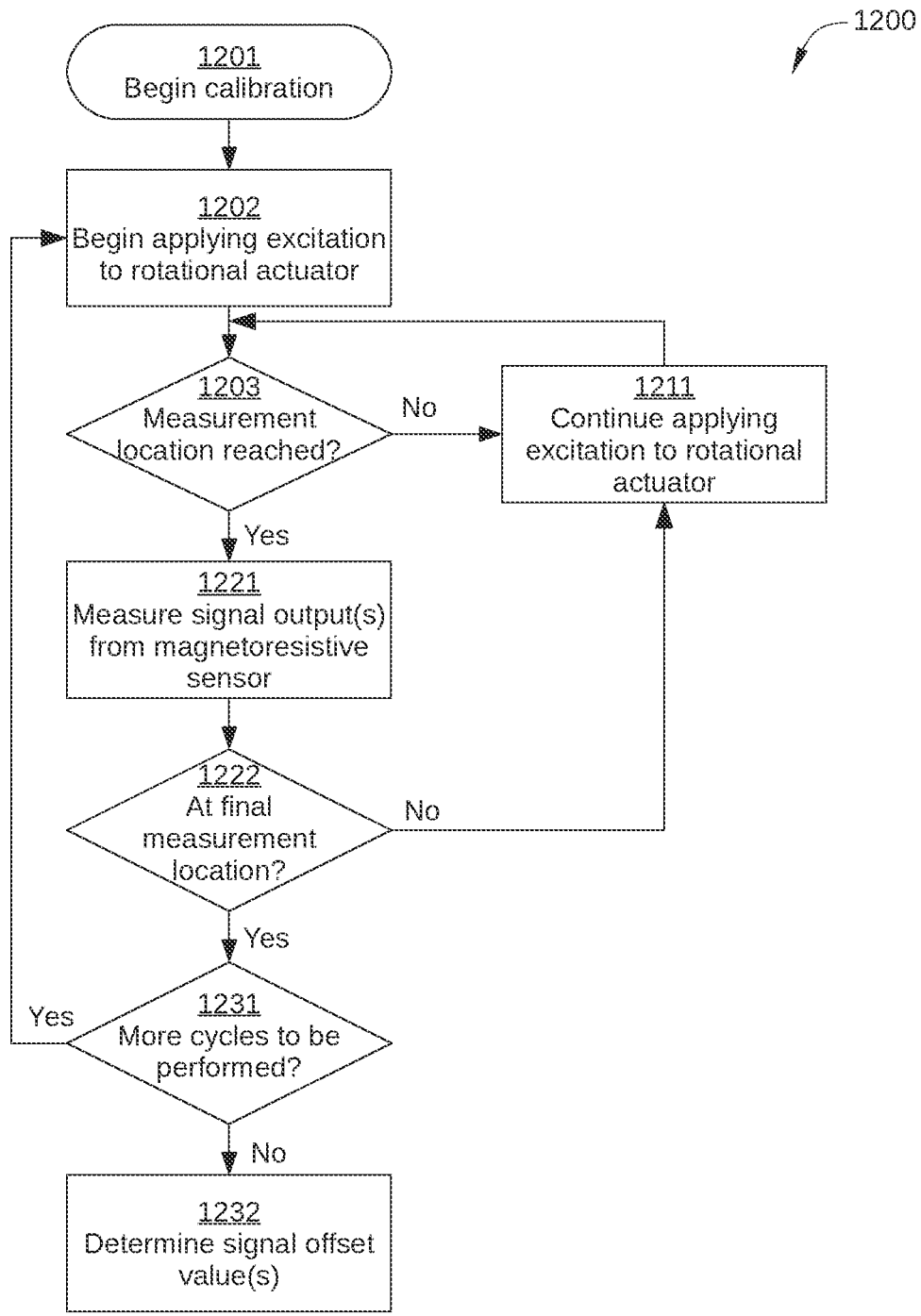
FIG. 12 sets forth a flowchart of a calibration process for rotational position detection via a magnetoresistive sensor, according to one or more embodiments.

FIG. 12 sets forth a flowchart of a calibration process for rotational position detection via a magnetoresistive sensor, according to one or more embodiments. The method may include one or more operations, functions, or actions as illustrated by one or more of blocks 1201-1232. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-11, persons skilled in the art will understand that any suitably configured radiation therapy system is within the scope of the present disclosure. In some embodiments, the control algorithms for the method steps may reside in image acquisition and treatment control computer 106, remote control console 110, or a combination of both. The control algorithms can be implemented in whole or in part as software- or firmware-implemented logic, and/or as hardware-implemented logic circuits.

A method 1200 begins at step 1201, when RT system 100 begins a calibration process. In some embodiments, method 1200 is performed a single time for a particular radiation therapy system, for example during commissioning, acceptance testing, and/or installation of the radiation therapy system. In alternative embodiments, method 1200 is performed periodically for a particular radiation therapy system, for example upon powering up of the radiation therapy system, upon completion of a specified duration of operation by the radiation therapy system, and/or upon completion of a specified number of procedures by the radiation therapy system.

In step 1202, RT system 100 begins applying an excitation to the rotational actuator configured to rotate MLC carousel 300 about axis of rotation 304. In some embodiments, the excitation may correspond to a rotational displacement of toothed ring 334 in which a first ferromagnetic tooth 1020 proximate magnetoresistive sensor 324 is rotated from a first rotational position to a second rotational position and a second ferromagnetic tooth 1020 that is adjacent to the first ferromagnetic tooth 1020 is rotated from the second rotational position to a third rotational position. One such specified rotational displacement is also referred to herein as an excitation cycle.

In step 1203, RT system 100 determines whether a measurement location has been reached. In some embodiments, a plurality of measurement locations are disposed across a specified rotational displacement, or excitation cycle. In one embodiment, 10s or 100s of measurement locations are passed through over the rotational displacement that corresponds to an excitation cycle. In such embodiments, a highly accurate curve of output vales for magnetoresistive sensor 324 can be generated across a single excitation cycle. As a result, an accurate signal offset value can be determined based on such a curve.

When RT system 100 determines that a measurement location has been reached, method 1200 proceeds to step 1221; when RT system 100 determines that a measurement location has not been reached, method 1200 proceeds to step 1211.

In step 1211, RT system 100 continues to apply the excitation to the rotational actuator and the rotational actuator continues to cause MLC carousel 300 (and toothed ring 334) to rotate.

In step 1221, RT system 100 measures one or more output signals from magnetoresistive sensor 324. In some embodiments, RT system 100 measures a sine output signal and a cosine output signal at the current rotational position. In some embodiments, RT system 100 measures multiple sine output signals (e.g., 4, 8, 10, etc.) and multiple cosine output signals (e.g., 4, 8, 10, etc.) at the current rotational position. In such embodiments, the multiple sine output signals are averaged to generate a single average sine output signal for the current rotational position, and the multiple cosine output signals are averaged to generate a single average cosine output signal for the current rotational position. It is noted that rotation of toothed ring 334 generally occurs at a relatively low rotational frequency (e.g. on the order of about 2 to 20 Hz). As a result, the multiple sine output signals and the multiple cosine output signals can be acquired sequentially during step 1221 at a sufficiently high acquisition rate that toothed ring 334 does not significantly rotate during step 1221. Thus, the multiple sine output signals and the multiple cosine output signals are effectively measured at the same rotational position.

In step 1222, RT system 100 determines whether the current rotational position of toothed ring 334 is at the final measurement location for the excitation cycle. If yes, method 1200 proceeds to step 1231; if no, method 1200 proceeds to step 1211.

In step 1231, RT system 100 determines whether additional excitation cycles are to be performed during the calibration process. In some embodiments, steps 1202-1222 are performed for a single excitation cycle. In other embodiments, steps 1202-1222 are performed for multiple excitation cycles, e.g., 2-5, so that signal offset values (e.g., for the sine output signal and the cosine output signal) can be averaged over the multiple excitation cycles. In yet other embodiments, steps 1202-1222 are performed for each ferromagnetic tooth 1020 of toothed ring 334. In such embodiments, a different signal offset value can be determined for rotational motion being measured between each ferromagnetic tooth 1020 of toothed ring 334. In such embodiments, each signal offset value can provide compensation for a different rotational position inaccuracy associated with the physical variations between ferromagnetic teeth 1020.

Figure 13:
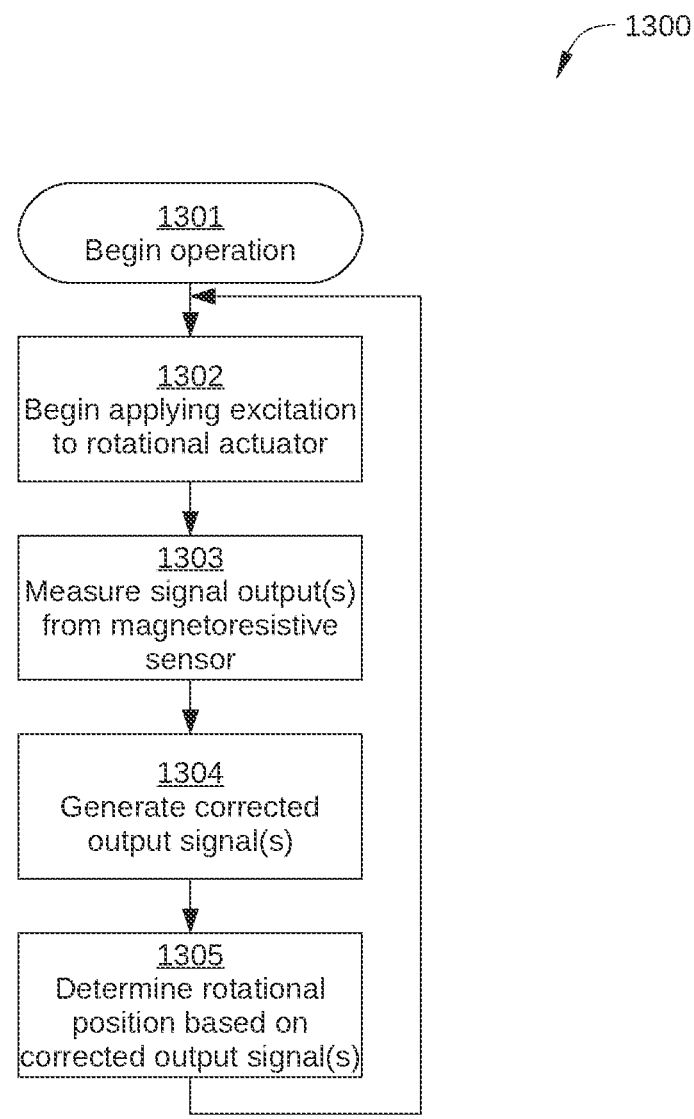
FIG. 13 sets forth a flowchart of a process for rotational position detection via a magnetoresistive sensor, according to one or more embodiments.

FIG. 13 sets forth a flowchart of a process for rotational position detection via a magnetoresistive sensor, according to one or more embodiments. The method may include one or more operations, functions, or actions as illustrated by one or more of blocks 1301-1305. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-12, persons skilled in the art will understand that any suitably configured radiation therapy system is within the scope of the present disclosure. In some embodiments, the control algorithms for the method steps may reside in image acquisition and treatment control computer 106, remote control console 110, or a combination of both. The control algorithms can be implemented in whole or in part as software- or firmware-implemented logic, and/or as hardware-implemented logic circuits.

A method 1300 begins at step 1301, when RT system 100 begins operation. For example, in one instance, MLC carousel 300 is rotated about axis of rotation 304 during a radiation therapy session.

In step 1302, RT system 100 begins applying an excitation to the rotational actuator configured to rotate MLC carousel 300 about axis of rotation 304.

In step 1303, RT system 100 measures one or more output signals from magnetoresistive sensor 324. In some embodiments, RT system 100 measures a sine output signal and a cosine output signal at the current rotational position.

In step 1304, RT system 100 generates one or more corrected output signals by modifying each of the one or more output signals measured in step 1303 with a corresponding signal offset value determined during a calibration process, such as method 1200. Thus, in some embodiments, a sine output signal measured in step 1303 is modified with a first signal offset value and a cosine output signal measured in step 1303 is modified with a second signal offset value.

In step 1305, RT system 100 determines a current rotational position of toothed ring 334 based on the one or more corrected output signals generated in step 1304.

After step 1305, method 1300 generally continues as RT system 100 rotates MLC carousel 300 during operation.

Figure 14:
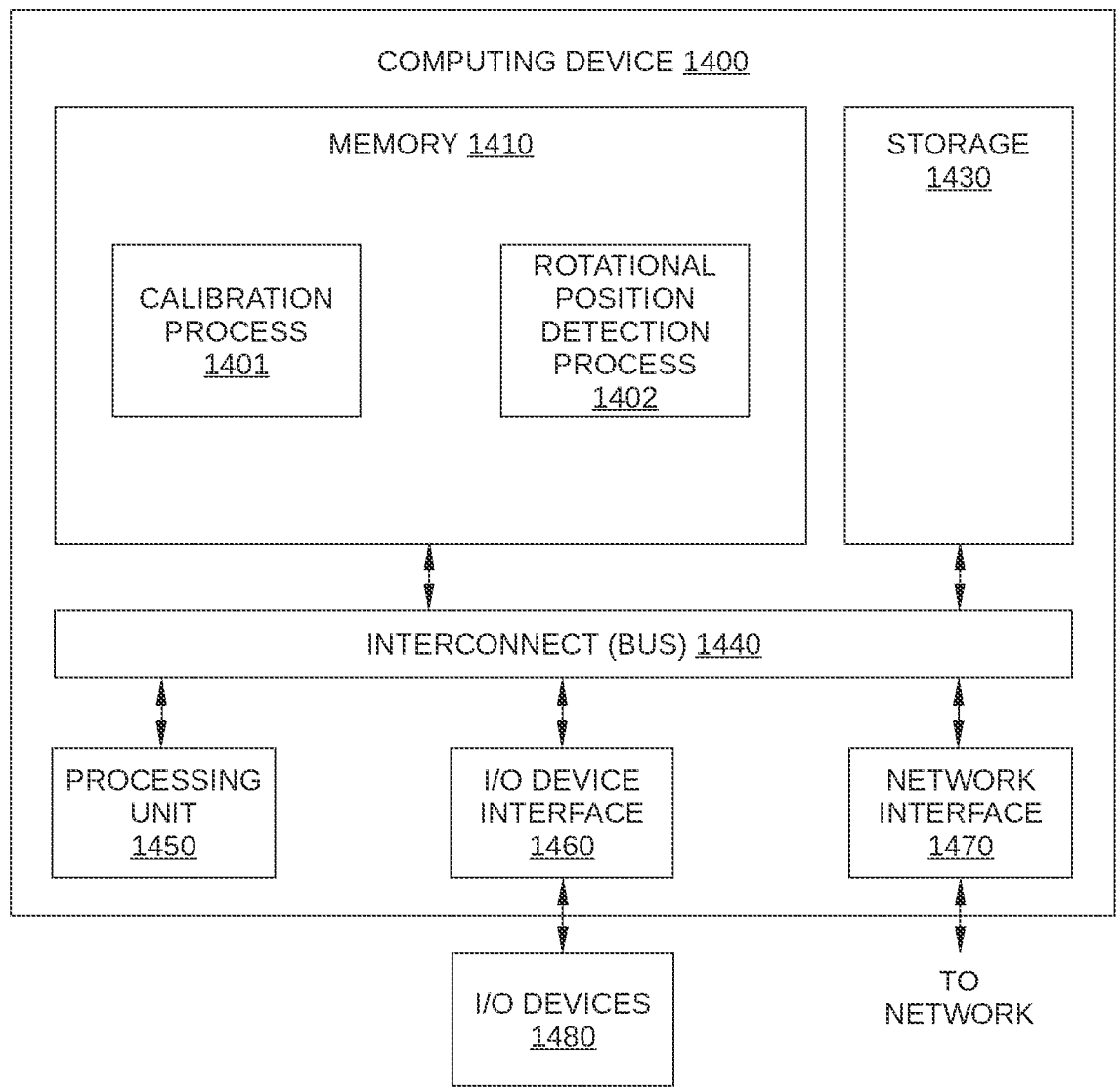
FIG. 14 is an illustration of computing device configured to perform various embodiments of the present disclosure.

FIG. 14 is an illustration of computing device 1400 configured to perform various embodiments of the present disclosure. Computing device 1400 may be a desktop computer, a laptop computer, a smart phone, or any other type of computing device suitable for practicing one or more embodiments of the present disclosure. For example, in some embodiments, computing device 1400 can be employed as image acquisition and treatment control computer 106 and/or remote control console 110. It is noted that the computing device described herein is illustrative and that any other technically feasible configurations fall within the scope of the present disclosure.

As shown, computing device 1400 includes, without limitation, an interconnect (bus) 1440 that connects a processing unit 1450, an input/output (I/O) device interface 1460 coupled to input/output (I/O) devices 1480, memory 1410, a storage 1430, and a network interface 1470. Processing unit 1450 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1450 may be any technically feasible hardware unit capable of processing data and/or executing software applications, including a calibration process 1401 consistent with method 1200 and/or a rotational position detection process 1402 consistent with method 1300.

I/O devices 1480 may include devices capable of providing input, such as a keyboard, a mouse, a touch-sensitive screen, and so forth, as well as devices capable of providing output, such as a display device and the like. Additionally, I/O devices 1480 may include devices capable of both receiving input and providing output, such as a touchscreen, a universal serial bus (USB) port, and so forth. I/O devices 1480 may be configured to receive various types of input from an end-user of computing device 1400, and to also provide various types of output to the end-user of computing device 1400, such as displayed digital images or digital videos. In some embodiments, one or more of I/O devices 1480 are configured to couple computing device 1400 to a network.

Memory 1410 may include a random access memory (RAM) module, a flash memory unit, or any other type of memory unit or combination thereof. Processing unit 1450, I/O device interface 1460, and network interface 1470 are configured to read data from and write data to memory 1410. Memory 1410 includes various software programs that can be executed by processor 1450 and application data associated with said software programs, including calibration process 1401 and/or rotational position detection process 1402.

Figure 15:
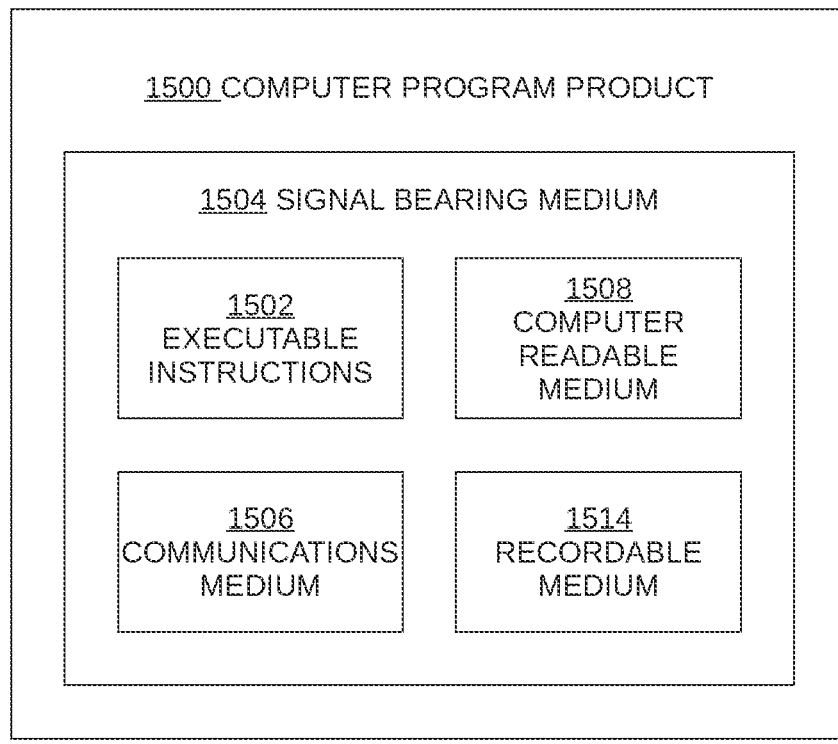
FIG. 15 is a block diagram of an illustrative embodiment of a computer program product for implementing various embodiments of the present disclosure.

FIG. 15 is a block diagram of an illustrative embodiment of a computer program product 1500 for implementing various embodiments of the present disclosure. Computer program product 1500 may include a signal bearing medium 1504. Signal bearing medium 1504 may include one or more sets of executable instructions 1502 that, when executed by, for example, a processor of a computing device, may provide at least the functionality described above with respect to FIGS. 1-14.

In some implementations, signal bearing medium 1504 may encompass a non-transitory computer readable medium 1508, such as, but not limited to, a hard disk drive, a Compact Disc (CD), a Digital Video Disk (DVD), a digital tape, memory, etc. In some implementations, signal bearing medium 1504 may encompass a recordable medium 1510, such as, but not limited to, memory, read/write (R/W) CDs, R/W DVDs, etc. In some implementations, signal bearing medium 1504 may encompass a communications medium 1506, such as, but not limited to, a digital and/or an analog communication medium (e.g., a fiber optic cable, a waveguide, a wired communications link, a wireless communication link, etc.). Computer program product 1500 may be recorded on non-transitory computer readable medium 1508 or another similar recordable medium 1510.

In sum, embodiments described herein enable precise and repeatable position measurement of an MLC and of the individual leaves of an MLC in a high-radiation environment. In addition, position measurement as described herein is non-contact, reducing wear-based inaccuracies and hysteresis.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A multileaf collimator carousel, comprising:
   at least one multileaf collimator layer that includes a plurality of leaves for shaping a radiotherapy beam, wherein each leaf in the plurality of leaves is independently movable in a linear travel direction;
   a first magnetoresistive sensor positioned to detect motion of the multileaf collimator carousel along a first axis of linear motion via a first linear array of magnets disposed on a first surface of the multileaf collimator carousel; and
   a second magnetoresistive sensor configured to detect motion of the multileaf collimator carousel along a second axis of linear motion via a second linear array of magnets disposed on a second surface of the multileaf collimator carousel.

2. The multileaf collimator carousel of claim 1, wherein the first axis of linear motion is perpendicular to the second axis of linear motion.

3. The multileaf collimator carousel of claim 1, wherein the first magnetoresistive sensor generates a first secondary motion detection signal associated with the multileaf collimator carousel and the second magnetoresistive sensor generates a second secondary motion detection signal associated with the multileaf collimator carousel.

4. The multileaf collimator carousel of claim 1, wherein each magnet included in the first linear array of magnets has a first magnetic moment that is oriented perpendicular to the first axis of linear motion.

5. The multileaf collimator carousel of claim 4, wherein each magnet included in the second linear array of magnets has a second magnetic moment that is oriented perpendicular to the second axis of linear motion.

6. The multileaf collimator carousel of claim 4, wherein each magnet included in the first linear array of magnets is adjacent to another magnet that is included in the first linear array of magnets and has a second magnetic moment that is oriented in an opposite direction to the first magnetic moment.

7. The multileaf collimator carousel of claim 1, wherein the first linear array of magnets is longitudinally oriented parallel to the first axis of linear motion.

8. The multileaf collimator carousel of claim 7, wherein the second linear array of magnets is longitudinally oriented parallel to the second axis of linear motion.

9. The multileaf collimator carousel of claim 1, wherein the at least one multileaf collimator layer includes a first multileaf collimator layer of leaves for shaping the radiotherapy beam and a second multileaf collimator layer of leaves for shaping the radiotherapy beam.

10. A method for measuring a location of a multileaf collimator carousel in a radiation therapy system, the method comprising:
receiving a first output from a first magnetoresistive sensor positioned to detect motion of the multileaf collimator carousel along a first axis of linear motion via a first linear array of magnets disposed on a first surface of the multileaf collimator carousel; and
based on the first output, determining a location of the multileaf collimator carousel in a travel direction parallel to the first axis of linear motion.

11. The method of claim 10, further comprising:
receiving a second output from a second magnetoresistive sensor positioned to detect motion of the multileaf collimator carousel along a second axis of linear motion via a second linear array of magnets disposed on a second surface of the multileaf collimator carousel; and
based on the first output, determining a location of the multileaf collimator carousel in a travel direction parallel to the second axis of linear motion.

12. The method of claim 11, wherein receiving the second output occurs concurrently with receiving the first output.

13. The method of claim 11, wherein the first axis of linear motion is perpendicular to the second axis of linear motion.

14. The method of claim 10, wherein the first linear array of magnets is longitudinally oriented parallel to the first axis of linear motion and the second linear array of magnets is longitudinally oriented parallel to the second axis of linear motion.

15. The method of claim 10, wherein determining a location of the multileaf collimator carousel in the travel direction parallel to the first axis of linear motion comprises determining a position of a particular magnet in the first linear array of magnets relative to the first magnetoresistive sensor.

16. A radiation therapy system, comprising:
a multileaf collimator carousel that includes:
at least one multileaf collimator layer that includes a plurality of leaves for shaping a radiotherapy beam, wherein each leaf in the plurality of leaves is independently movable in a linear travel direction;
a first magnetoresistive sensor positioned to detect motion of the multileaf collimator carousel along a first axis of linear motion via a first linear array of magnets disposed on a first surface of the multileaf collimator carousel; and
a second magnetoresistive sensor configured to detect motion of the multileaf collimator carousel along a second axis of linear motion via a second linear array of magnets disposed on a second surface of the multileaf collimator carousel; and
a radiation source for generating the radiotherapy beam.

17. The radiation therapy system of claim 16, further comprising a controller configured to perform the steps of:
receiving a first output from the first magnetoresistive sensor; and
based on the first output, determining a location of the multileaf collimator carousel in a travel direction parallel to the first axis of linear motion.

18. The radiation therapy system of claim 16, wherein the first axis of linear motion is perpendicular to the second axis of linear motion.

19. He radiation therapy system of claim 16, wherein each magnet included in the first linear array of magnets has a first magnetic moment that is oriented perpendicular to the first axis of linear motion.

20. The radiation therapy system of claim 16, wherein the first linear array of magnets is longitudinally oriented parallel to the first axis of linear motion.

* * * * *